United States Patent
Zhang et al.

(10) Patent No.: US 10,156,572 B2
(45) Date of Patent: Dec. 18, 2018

(54) THREE ARM Y-SHAPED BISBIOTIN LIGAND

(71) Applicant: Arizona Board of Regents on behalf of Arizona State University, Scottsdale, AZ (US)

(72) Inventors: Peiming Zhang, Gilbert, AZ (US); Stuart Lindsay, Phoenix, AZ (US); Subhadip Senapati, Tempe, AZ (US); Sudipta Biswas, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 15/119,549

(22) PCT Filed: Feb. 18, 2015

(86) PCT No.: PCT/US2015/016411
§ 371 (c)(1),
(2) Date: Aug. 17, 2016

(87) PCT Pub. No.: WO2015/126963
PCT Pub. Date: Aug. 27, 2015

(65) Prior Publication Data
US 2017/0067902 A1 Mar. 9, 2017

Related U.S. Application Data

(60) Provisional application No. 61/941,141, filed on Feb. 18, 2014.

(51) Int. Cl.
*C12Q 1/68* (2018.01)
*G01N 33/58* (2006.01)
*C07C 247/04* (2006.01)
*C07D 495/04* (2006.01)
*C12Q 1/6816* (2018.01)
(Continued)

(52) U.S. Cl.
CPC ......... *G01N 33/587* (2013.01); *C07C 247/04* (2013.01); *C07D 495/04* (2013.01); *C12Q 1/6816* (2013.01); *C12Q 1/6834* (2013.01); *G01N 33/58* (2013.01); *G01Q 60/38* (2013.01)

(58) Field of Classification Search
CPC .................................................. G01N 33/587
USPC .......................................... 536/26.6; 435/6.1
See application file for complete search history.

(56) References Cited

U.S. PATENT DOCUMENTS

| | | |
|---|---|---|
| 7,247,384 B2 | 7/2007 | Cai et al. |
| 8,628,649 B2 | 1/2014 | Lindsay et al. |
| 8,961,757 B2 | 2/2015 | Nuckolls et al. |

(Continued)

FOREIGN PATENT DOCUMENTS

| | | |
|---|---|---|
| WO | 2013184796 | 12/2013 |

OTHER PUBLICATIONS

S. T. Kim et al. Novel streptavidin-functionalized silicon nanowire arrays for CD4+ T lymphocyte separation. Nano letters 2010, 10, 2877-2883.

(Continued)

*Primary Examiner* — Jezia Riley
(74) *Attorney, Agent, or Firm* — Schwabe, Williamson & Wyatt, P.C.

(57) ABSTRACT

Embodiments of the present disclosure provide bisbiotin ligands and related conjugates and methods. The bisbiotin ligands, combined with streptavidin, can be used in the separation, labelling, targeting, and immobilization of biomolecules.

17 Claims, 15 Drawing Sheets

(51) Int. Cl.
 C12Q 1/6834 (2018.01)
 G01Q 60/38 (2010.01)

(56) References Cited

U.S. PATENT DOCUMENTS

| | | | |
|---|---|---|---|
| 8,968,540 | B2 | 3/2015 | Reinhart et al. |
| 9,140,682 | B2 | 9/2015 | Lindsay et al. |
| 9,274,430 | B2 | 3/2016 | Gyarfas et al. |
| 9,395,352 | B2 | 7/2016 | Lindsay et al. |
| 9,593,372 | B2 | 3/2017 | Lindsay et al. |
| 9,766,248 | B2 | 9/2017 | Lindsay et al. |
| 9,810,681 | B2 | 11/2017 | Lindsay et al. |
| 2009/0326238 | A1 | 12/2009 | Burn et al. |
| 2012/0288935 | A1 | 11/2012 | Mirkin et al. |
| 2013/0302901 | A1 | 11/2013 | Lindsay et al. |
| 2013/0316912 | A1 | 11/2013 | Bjornson et al. |
| 2015/0010935 | A1 | 1/2015 | Lindsay et al. |
| 2015/0142327 | A1 | 5/2015 | Ashcroft et al. |
| 2015/0144506 | A1 | 5/2015 | Lindsay et al. |
| 2016/0018384 | A1 | 1/2016 | Lindsay et al. |
| 2016/0108002 | A1 | 4/2016 | Zhang et al. |
| 2016/0177383 | A1 | 6/2016 | Ashcroft et al. |
| 2016/0194698 | A1 | 7/2016 | Lindsay |
| 2016/0258925 | A1 | 9/2016 | Gyarfas et al. |
| 2016/0280723 | A1 | 9/2016 | Zhang et al. |
| 2017/0003245 | A1 | 1/2017 | Lindsay et al. |
| 2017/0016852 | A1 | 1/2017 | Lindsay et al. |
| 2017/0038369 | A1 | 2/2017 | Lindsay et al. |
| 2017/0137389 | A1 | 5/2017 | Zhang et al. |
| 2017/0204066 | A1 | 7/2017 | Lindsay et al. |
| 2017/0343558 | A1 | 11/2017 | Lindsay et al. |

OTHER PUBLICATIONS

J. Spinke et al. Molecular recognition at self-assembled monolayers: The construction of multicomponent multilayers. Langmuir: the ACS journal of surfaces and colloids 1993, 9, 1821-1825.
S. A. Walper et al. Comparison of single domain antibody immobilization strategies evaluated by surface plasmon resonance. J Immunol Methods 2013, 388, 68-77.
D. Yamamoto et al. Streptavidin 2D crystal substrates for visualizing biomolecular processes by atomic force microscopy. Biophys J 2009, 97, 2358-2367.
J. P. Ross et al. Identification of differentially methylated regions using streptavidin bisulfite ligand methylation enrichment (SuBLiME), a new method to enrich for methylated DNA prior to deep bisulfite genomic sequencing. Epigenetics: official journal of the DNA Methylation Society 2013, 8, 113-127.
M. S. Akhras et al. The sequencing bead array (SBA), a next-generation digital suspension array. PLoS One 2013, 8, e76696.
L. P. Rodriguez et al. Development of a solid-phase receptor-based assay for the detection of cyclic imines using a microsphere flow cytometry system. Anal Chem 2013, 85, 2340-2347.
Z. Cao et al. Modulation of glycan detection on specific glycoproteins by lectin multimerization. Anal Chem 2013, 85, 1689-1698.
K. Tanaka et al. Cell surface biotinylation by azaelectrocyclization: Easy-handling and versatile approach for living cell labeling. Bioorg Med Chem 2012, 20, 1865-1868.
H. B. Breitz et al. Clinical optimization of pretargeted radioimmunotherapy with antibody-streptavidin conjugate and 90Y-DOTA-Biotin. J Nucl. Med 2000, 41, 131-140.
E. Frampas et al. Improvement of radioimmunotherapy using pretargeting. Frontiers in oncology 2013, 3, 159.
J. Bushman et al. Functionalized nanospheres for targeted delivery of paclitaxel. Journal of controlled release 2013, 171, 315-321.
P. Ringler et al. Self-assembly of proteins into designed networks. Science 2003, 302, 106-109.
T. Bing et al. Specific interactions between adenosine and streptavidin/avidin. Bioorg Med Chem Lett 2012, 22, 7052-7055.
M. Fukuto et al. Effects of surface ligand density on lipid-monolayer-mediated 2D assembly of proteins. Soft Matter 2010, 6, 1513.
D. Dressman et al. Transforming single DNA molecules into fluorescent magnetic particles for detection and enumeration of genetic variations. Proceedings of the National Academy of Sciences of the United States of America 2003, 100, 8817-8822.
D. S. Wilbur et al. Biotin reagents for antibody pretargeting. 2. Synthesis and in vitro evaluation of biotin dimers and trimers for cross-linking of streptavidin. Bioconjugate Chem. 1997, 8, 819-832.
K. J. Hamblett et al. Role of Biotin-binding affinity in streptavidin-based pretargeted radioimmunotherapy of lymphoma. Bioconjugate Chem. 2005, 16, 131-138.
S. Burazerovic et al. Hierarchical self-assembly of one-dimensional streptavidin bundles as a collagen mimetic for the biomineralization of calcite. Angew Chem Int Ed Engl 2007, 46, 5510-5514.
K. Oohora et al. Chemically programmed supramolecular assembly of hemoprotein and streptavidin with alterating alignment. Angew Chem Int Ed Engl 2012, 51, 3818-3821.
Y. Mori et al. Protein supramolecular complex formation by site-specific avidin-biotin interactions. Org Biomol Chem 2013, 11, 914-922.
H. Wang et al. Glutaraldehyde modified mica: a new surface for atomic force microscopy of chromatin. Biophysical J., 2002, 83, 3619-3625.
Wilbur et al. Development of new biotin:streptavidin reagents for pretargeting. Biomolecular engineering 1999, 16, 113-118.
International search report with written opinion for international application PCT/US15/16411 filed on Feb., 18, 2015.

8

THREE ARM Y-SHAPED BISBIOTIN LIGAND

CROSS-REFERENCE TO RELATED APPLICATIONS

This application is a U.S. national phase of PCT/US2015/016411, filed Feb. 18, 2015 and claims the benefit of and priority to U.S. Provisional Application No. 61/941,141 titled "A THREE ARM Y-SHAPED BISBIOTIN LIGAND", filed Feb. 18, 2014, the entire disclosures of which is incorporated herein by reference in their entireties.

FIELD OF THE DISCLOSURE

The present disclosure relates generally to bisbiotin ligands that form stable complexes with streptavidin, which can be used in isolation of DNA and proteins, biomolecular labeling, immobilization in the biotechnology field, PCR technology, fabrication of bioassays, magnetic bead based separation and/or development of self-assembled protein biomaterials.

BACKGROUND OF THE DISCLOSURE

The bond between biotin and streptavidin is one of the strongest known non-covalent interactions with a $K_d$ of $\sim 10^{-14}$ M. This interaction has been developed into a streptavidin-biotin technology by functionalizing either or both of these two molecules, thereby allowing for targeting, labelling and tagging of a specific molecule. Streptavidin-biotin technology is a cornerstone of bin-assays, biomolecule purification, biomolecule immobilization, and cell separation in biotechnology and nanobiotechnology (See S. T. Kim et al., Nano Letters, 2010, 10, 2877-2833 for example). In the streptavidin-biotin technology, streptavidin is used as an anchor molecule to attach a biotinylated probe, receptor, ligand, antibody, and aptamer to a surface. (See J. Spinke et al., Langmuir, 1993, 9, 1821-1825; S. A. Walper et al., J Immunol Methods, 2013, 388, 68-77).

Streptavidin-biotin technology has also been used to form streptavidin 2D crystal substrates for visualizing biomolecular processes with Atomic Force Microscopy. (See D. Yamamoto et al., Biophys J., 2009, 97, 2358-2367). In one example of the streptavidin-biotin technology, streptavidin coated magnetic beads have been used in separation and analysis of biotinylated DNA samples. (See J. P. Ross et al., Epigenetics, 2013, 8, 113-127; M. S. Akhras et al., PLoS One, 2013, 8, e76696). Additionally, the technology has also been used as a linker to form multivalent ligands to enhance the lectin glycan interaction (see L. P. Rodriguez et al., Anal Chem, 2013, 85, 2340-2347) and in pretargeting for radioimmunotherapy (see H. B. Breitz et al., J Nucl. Med, 2000, 41, 131-140; E. Frampas, Frontiers in oncology, 2013, 3, 159.) and drug delivery (see J. Bushman et al., Journal of controlled release, 2013). Moreover, a dye labeled streptavidin may be used as a reagent for bioassays (see Z. Cao et al., Anal Chem, 2013, 85, 2340-2347) and as a marker for biotinylated cells in cell culture (see K. Tanaka et al., Bioorg Med Chem, 2012, 20, 1865-1868). In another example, the streptavidin-biotin technology has also been used in self-assembly of protein networks (See P. Ringler et al., Science, 2003, 302, 106-109) which may simplify development of new nanomaterials.

Dual biotinylated oligonucleotides were immobilized on streptavidin coated magnetic beads for PCR assays, yet some of the oligonucleotides dissociated from the beads during the thermal cycling (See D. Dressman et al., PNAS, 2003, 100, 8817-8822), Biotin dimers and trimers have been synthesized using PEG as linkers and assayed for their ability to crosslink streptavidin, and, thus, for their potential to be used to increase the amount of radioactivity on cancer cells in tumor pretargeting protocols. (See D. S. Wilbur et al., Bioconjugate Chem, 1997, 8, 819-832). A bisbiotin reagent has been used to improve efficacy of the pretargeting tumor treatment. (See K. J. Hamblett et al., Bioconjugate Chem., 2005, 16, 131-138). A ferrous complex containing two bisbiotin moieties forms a one-dimensional metal-organic framework with streptavidin as a collagen mimetic for the biomineralization of calcite. (See S. Burazerovic et al., Angew Chem Int Ed Engl, 2007, 46, 5510-5514). A heme-bisbiotin trifunctional linker has been reported as a prosthetic group capable of assembling one dimensional protein fibers. (See FIG. 2 of K. Oohara et al., Angnew Chem Int Ed Engl, 2012, 51, 3818-3821). In addition, a flexible bisbiotin peptide linker attached to alkaline phosphatase forms the ring shaped complexes with streptavidin. (see Y. Mori et al., Org Biomol Chem, 2013, 11, 914-922).

Accordingly, the potential for bisbiotin linkers is vast. However, known bisbiotin linkers lack demonstrable thermal stability. Accordingly, there remains a need in the art for thermostable bisbiotin linkers.

SUMMARY OF THE DISCLOSURE

Described herein are three arm bisbiotin ligands that can form a streptavidin-biotin complex with high thermal stability and slow dissociation rate. Streptavidin-biotin complexes of embodiments of the present disclosure retain stability even in the presence of micromolar concentrations of biotin solution (where monobiotin complexes are rapidly dissociated). Thus, the bisbiotin ligands of some of the embodiments of the present disclosure form more stable complexes than those formed by monobiotin ligands binding streptavidin.

The tri-linker of the present disclosure allows for two biotin moieties to be covalently joined and further, linked to a head group that can be readily conjugated to a tag, marker, molecule of interest, or other. These bisbiotin molecules show increased thermal stability, increased bond strength, and slowed dissociation in complex with streptavidin when compared to the equivalent number of mono-biotin moieties.

Compounds of some of the embodiments of the present disclosure may be used in PCR technologies for amplification or for Real Time PCR, fabrication of bioarrays, and magnetic bead separation. In some embodiments, compounds may also be immobilized on a solid substrate and used to capture streptavidin and its conjugates, Alternatively, a substrate may contain streptavidin. For example, streptavidin can be immobilized onto a mica substrate and biotin compounds of some of the embodiments of the present disclosure can be bound thereto.

By way of non-limiting examples, stable localization of conjugate molecules in this way provides a means for structural studies, binding or capture assays and sequencing or imaging arrays.

The bisbiotin compounds according to embodiments of the present disclosure may be conjugated to any molecules of interest including, but not limited to, fluorescent dyes, substrates, films, nucleic acid probes, small molecule ligands, proteins, peptides, magnetic beads, nanoparticles, etc.

Some embodiments of the present disclosure provide ligands containing a multiplicity of biotin moieties, wherein each biotin moiety is attached to a rigid, nanometer central core through a flexible linker wherein the ligand presents at least two biotin moieties to a target. For example, the target is streptavidin. In some embodiments of the present disclosure, two biotin moieties are attached to a central trilinker to form bisbiotin compounds. Various structures of the trilinker are disclosed herein. For example, the trilinker can have the structure of formulas I, II, or III.

In any of the trilinkers described herein n may be any integer between 1 and 50. Those skilled in the art will recognize that the amines in the trilinker of structure I may be replaced by a thiol, oxyamine, or any other reactive groups orthogonal to the azide. For example, a ligand of some of the embodiments of the present disclosure may have the structure of formula IV.

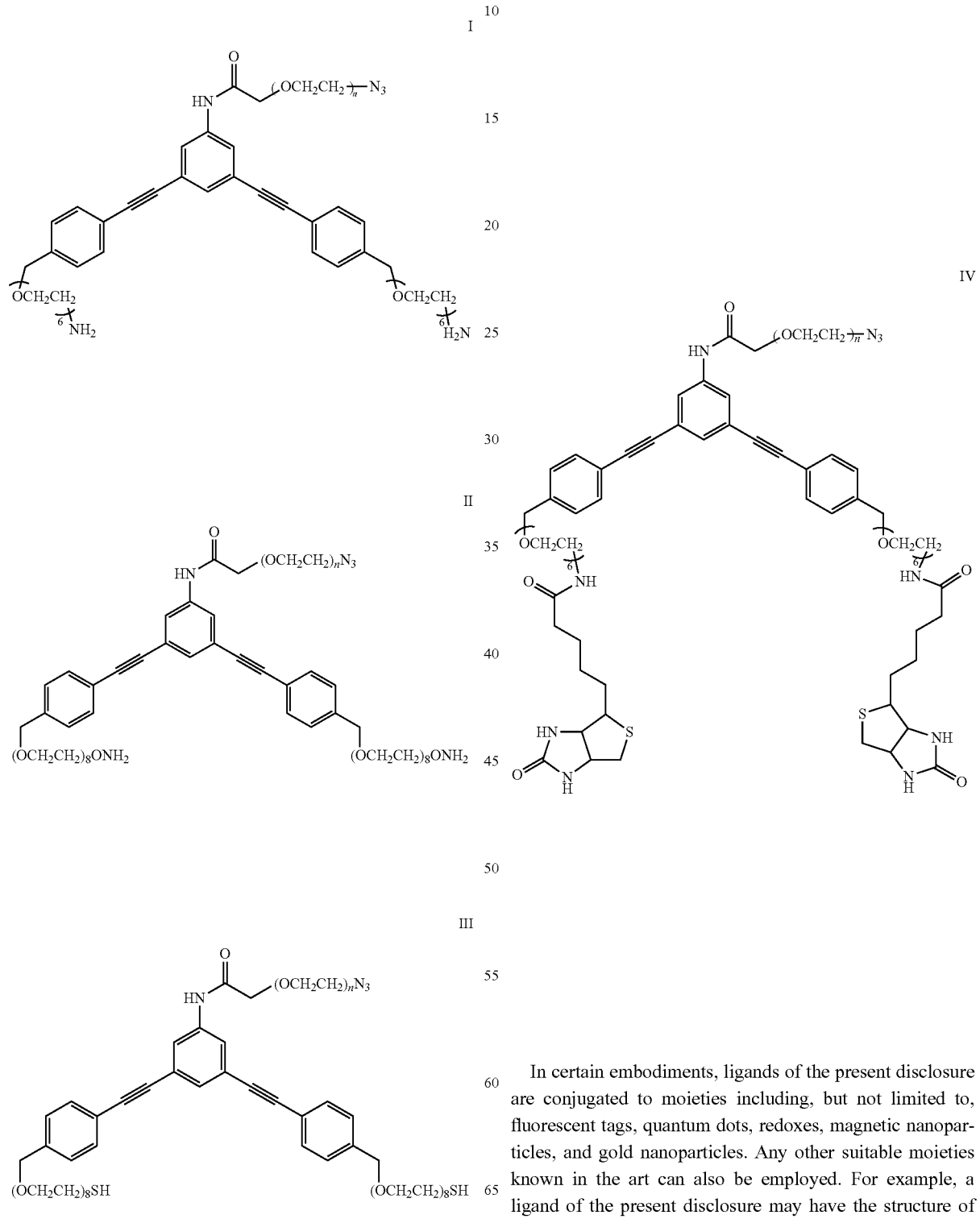

In certain embodiments, ligands of the present disclosure are conjugated to moieties including, but not limited to, fluorescent tags, quantum dots, redoxes, magnetic nanoparticles, and gold nanoparticles. Any other suitable moieties known in the art can also be employed. For example, a ligand of the present disclosure may have the structure of formula V.

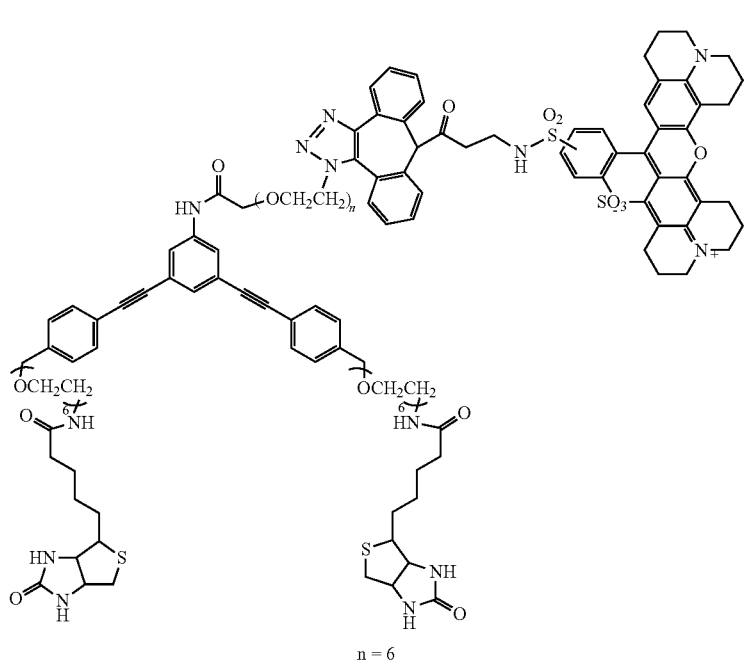

V

In certain embodiments, ligands of the present disclosure are immobilized to an atomic force microscopy tip e.g., in order to attach streptavidin followed by biotinylated antibodies and other affinity molecules. For example, the ligand may be connected to the atomic force microscopy tip via a PEG linker.

In certain embodiments, a ligand of the present disclosure may be attached to nanoparticles functionalized with alkynes in a method for the separation and detection of biomolecules including DNA, RNA, proteins, peptides, and the like.

Also provided are methods for the separation and detection of biomolecules (e.g., DNA, RNA, proteins, and/or peptides) by immobilizing streptavidin to a bisbiotin linker according to some embodiments of the present disclosure that is attached to nanoparticles functionalized with alkynes; attaching one or more biotinylated probes (e.g., DNA probes and/or RNA probes) or affinity molecules (e.g., antibodies, aptamers, or peptides) to form a streptavidin/biotin nanoparticle complex; incubating the nanoparticle complex with a biological sample under conditions to allow the nanoparticle complex to bind to biomolecules in a biological sample; detecting the binding of biomolecules to the nanoparticle complex; and separating the biomolecules bound to the nanoparticle complex from the biological sample. Those skilled in the art will recognize that the biotinylated DNA probes and/or affinity molecules may also be conjugated with any of the ligands described herein.

In certain embodiments, a ligand of the present disclosure may have a thiol group at a non-biotin moiety region of the ligand. For example, the ligand may have the structure of formula VI.

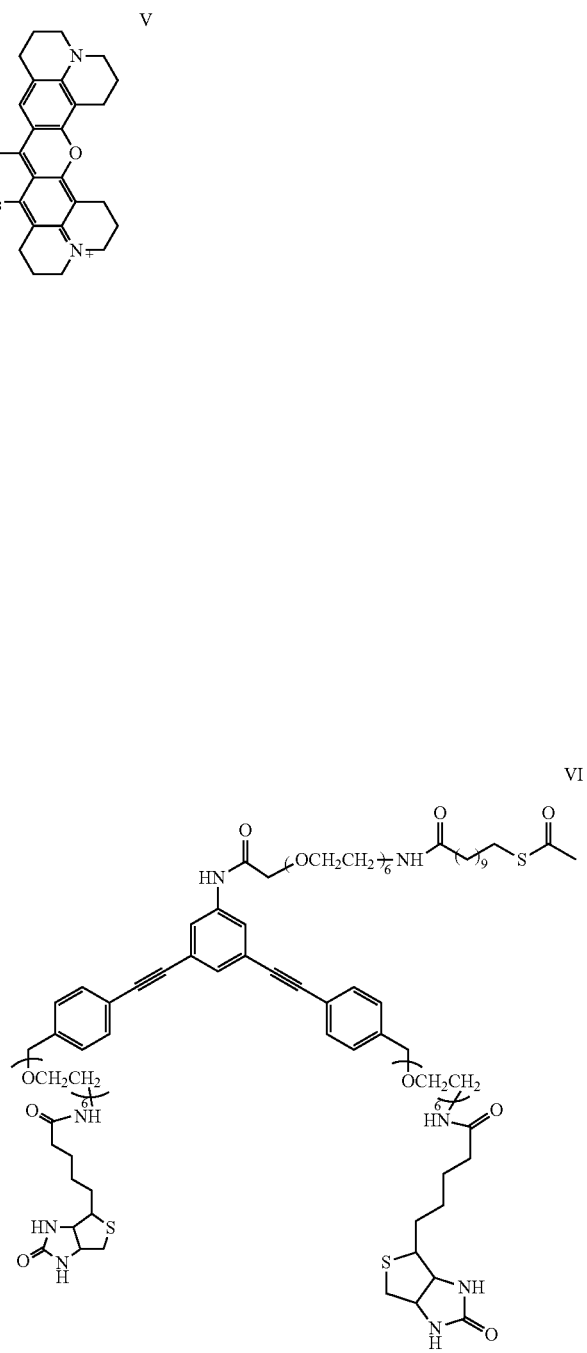

VI

In certain embodiments, a ligand of the present disclosure may be immobilized on a gold substrate to form a monolayer. For example, a gold monolayer containing a ligand of the present disclosure may also have an alkylated PEG spacer.

DETAILED DESCRIPTION

The details of embodiments of the present disclosure have been set forth in the accompanying description below. Although any methods and materials similar or equivalent to those described herein can be used in the practice or testing of the present disclosure, the preferred methods and materials are now described, Other features, objects, and advantages of the present disclosure will be apparent from the description and from the claims. In the specification and the appended claims, the singular forms include plural references unless the context clearly dictates otherwise. All patents and publications cited in this specification are incorporated by reference in their entirety. Unless otherwise defined, all technical and scientific terms used herein have the same meaning as commonly understood by one of ordinary skill in the art to which embodiments of the present disclosure pertain.

Streptavidin interacts with other small molecules such as adenosine, which may result in non-specific interactions in the presence of unoccupied biotin binding sites. (See T. Bing et al., Bioarg Med Chem Lett, 2012, 22, 7052-7055). The four high-affinity binding sites of streptavidin can bind multiple biotinylated ligands and cause target aggregation. However, because protein aggregation can change its biological functions, the use of streptavidin in live cells can be prone to artifacts. The doubly bound form of streptavidin (SA-$b_2$) is required to form a 2D crystal on a biotin bearing lipid monolayer. (See M. Fukuto et al., Soft Matter, 2010, 6, 1513).

Figure 1:
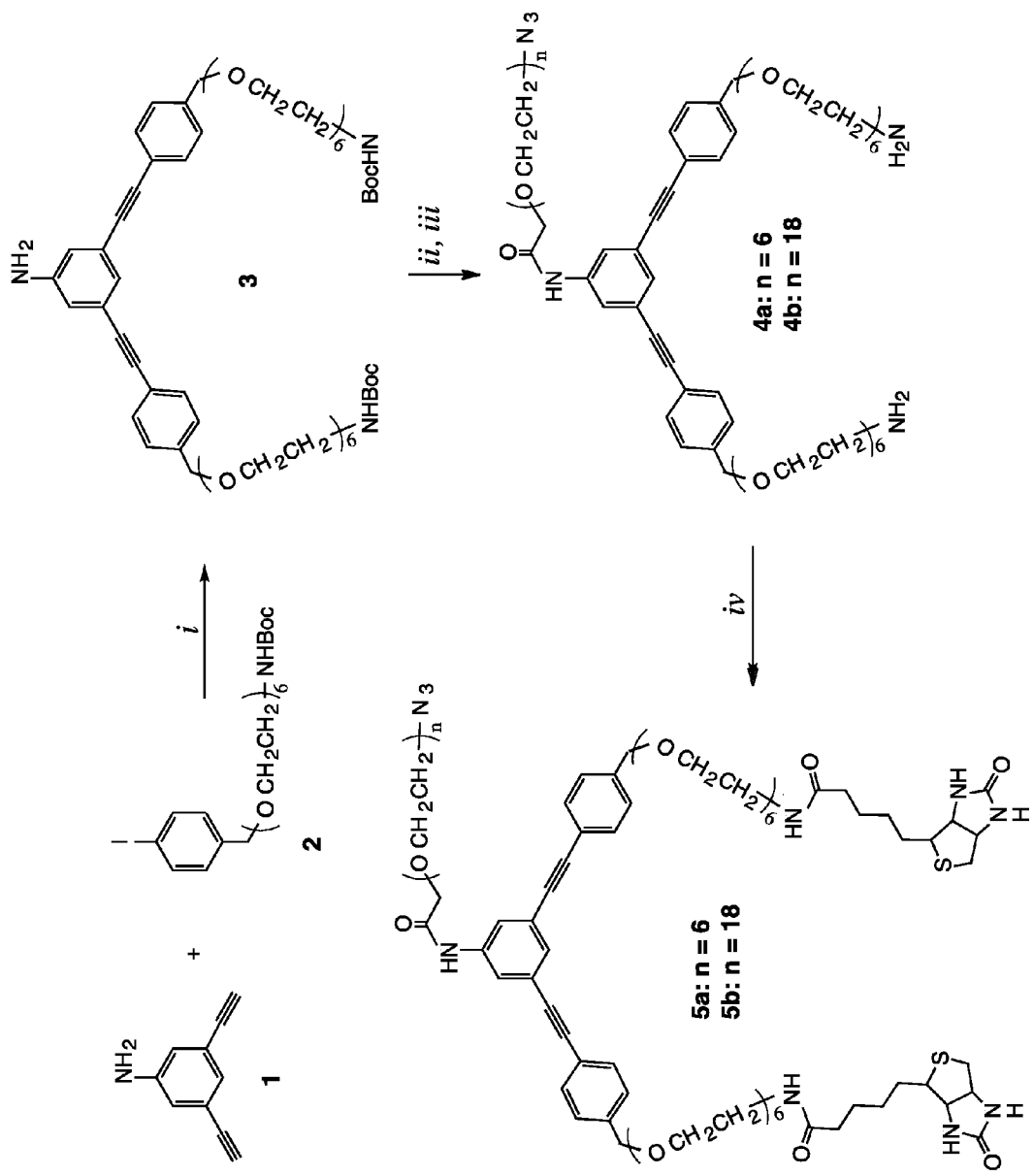
FIG. 1 shows the synthesis of three arm bisbiotin ligands (5a) and (5b).
Figure 2:
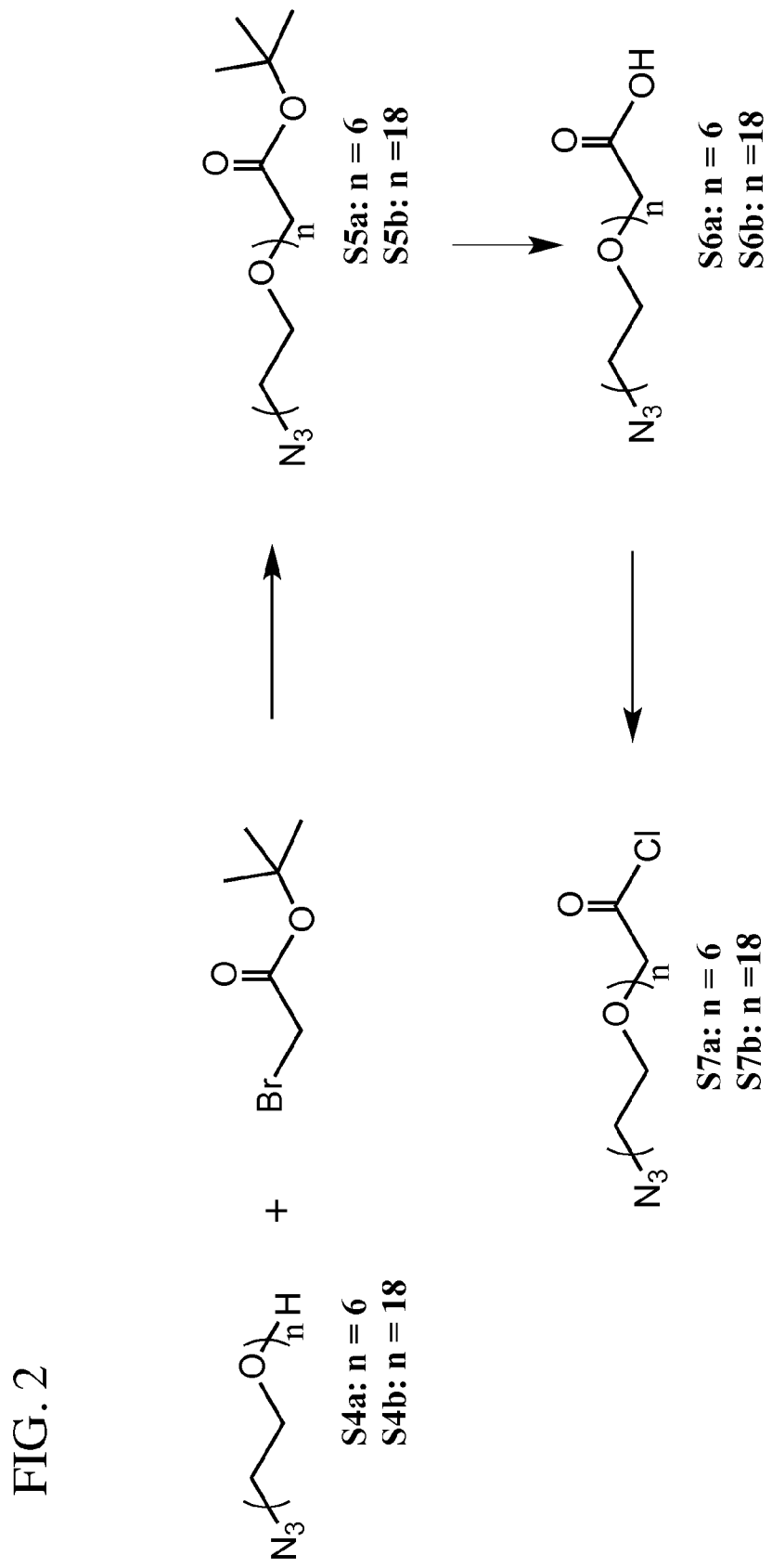
FIG. 2 shows the synthesis of starting materials S7a and S7b used in the synthesis shown in FIG. 1.
Figure 3:
FIG. 3 shows a simulated conformation of the (5a) bisbiotin ligand calculated by density functional theory (DFT).

A class of three-arm bisbiotin ligands, (5a) and (5b), are synthesized as outlined in FIG. 1. In these reactions, reagents and conditions are as follows: (i) Pd(PPh3)Cl2, CuI, THE Et3N=1:1, rt, 5 h; (ii) S7a or S7b, pyridine, dichloromethane, rt, 12 h; (iii) trifluoroacetic acid, rt, 10 min; (iv) biotin N-hydroxysuccinimide ester, triethylamine, DMF, rt, 3 h. The synthesis of starting materials S7a and S7b used in an intermediate reaction of the synthesis shown in FIG. 1 is shown in FIG. 2, FIG. 3 shows a Y shaped conformation of bisbiotin ligand (5a) generated from computation software Spartan'14 (Wavefunction Inc.). First, the 2D chemical structures were drawn in ChemBioDraw Ultra 11 and exported to Spartan'14 to generate a 3D structure that was subjected to energy minimization using the built-in MMFF94s molecular mechanics, and then the structure was optimized using the DFT (Density Functional Theory) calculation, B3LYP with basis set 6-31+G* in vacuum.

Figure 4:
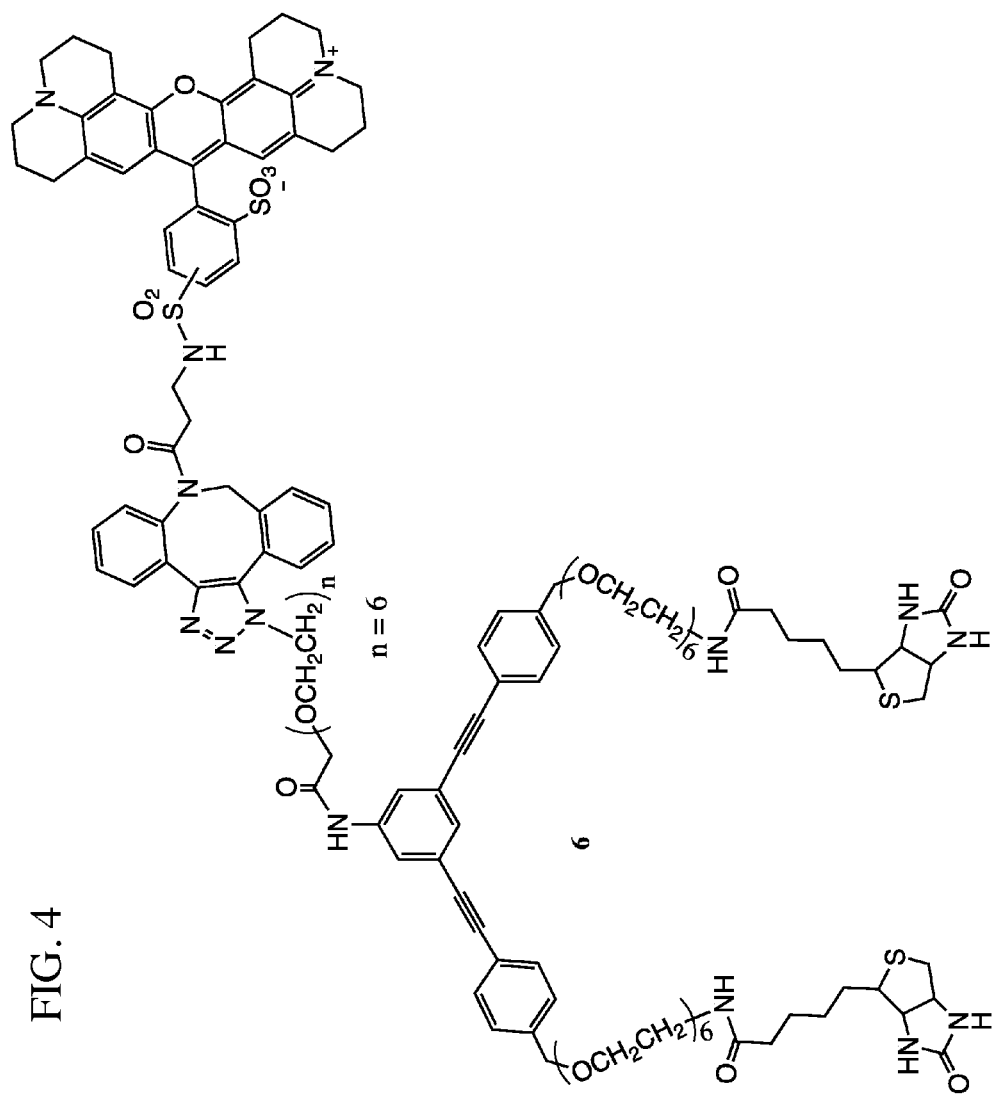
FIG. 4 shows the chemical structure of a conjugate (6) of the three arm bisbiotin ligand (5a) with a fluorescent dye (DBCO-Fluor 585 from KeraFast®).
Figure 5:
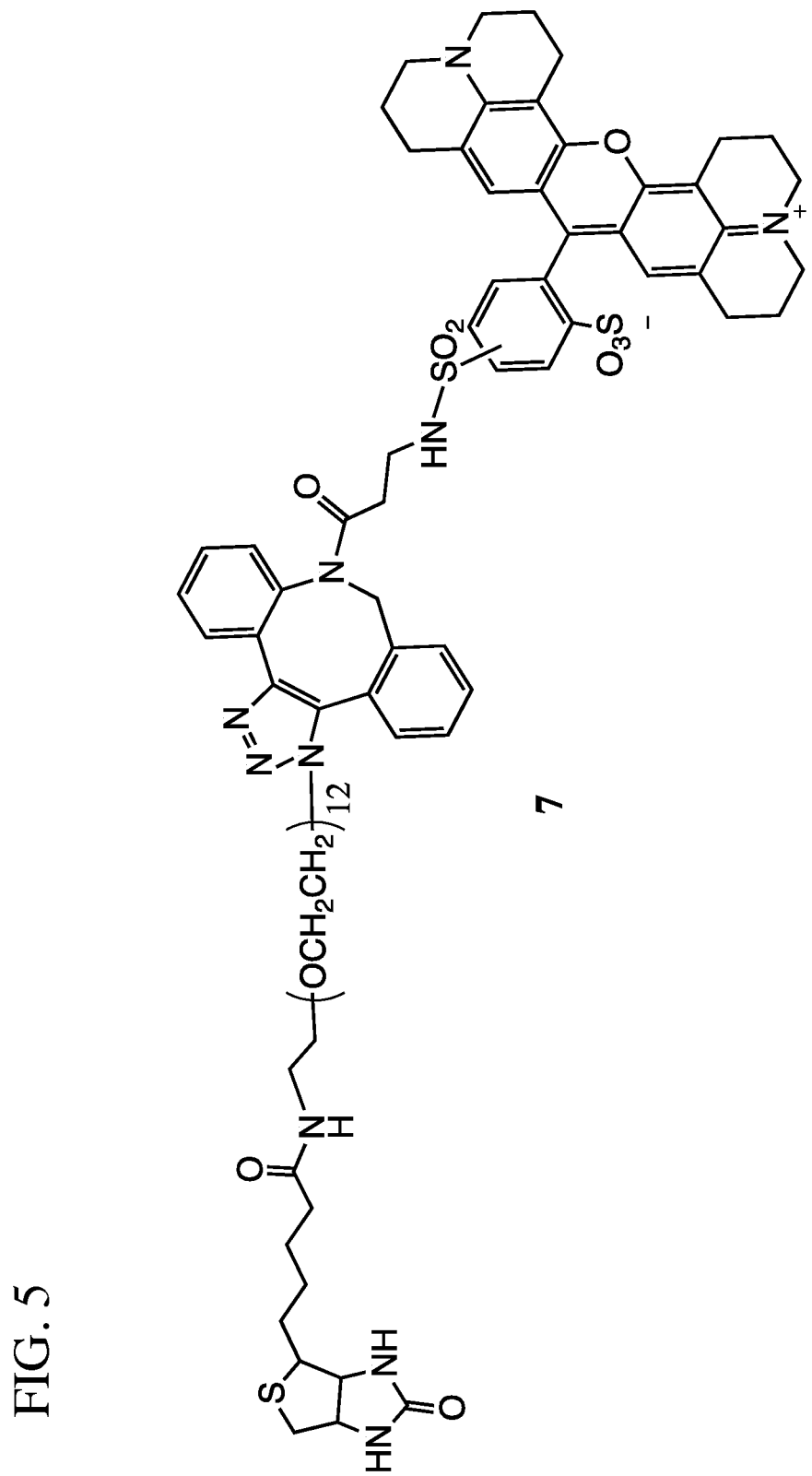
FIG. 5 shows the chemical structure of a conjugate (7) of mono-biotin ligand with a fluorescent dye (DBCO-Fluor 585 from KeraFast®).

The structure of conjugate (6), a three-arm bisbiotin ligand (5a) conjugated with a fluorescent dye DBCO-Fluor 585 (from KeraFast®) is shown in FIG. 4. A conjugate (7) of mono-biotin with DBCO-Fluor 585 was also synthesized and used as a positive control (see FIG. 5).

Figure 6:
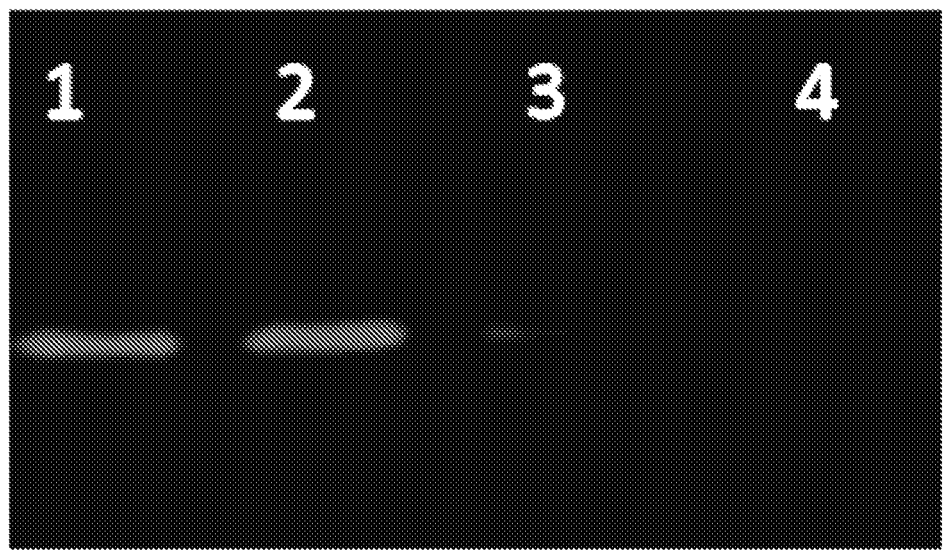
FIG. 6 shows an image of an SDS-polyacrylamide gel electrophoresis of complexes of streptavidin with bisbiotin ligand (6) and mono-biotin ligand (7), demonstrating that the bisbiotin ligand can form a 1:1 complex with streptavidin. Lane 1 shows streptavidin incubated with fluorescent labelled mono-biotin (7) in a 1:2 ratio at room temperature; Lane 2 shows streptavidin with fluorescently labelled bisbiotin (6) in a 1:1 ratio at room temperature; Lane 3 shows streptavidin with fluorescent dye (DBCO-Fluor 585 from KeraFast®, negative control); and Lane 4 shows streptavidin alone.

FIG. 6 is an image of gel electrophoresis of streptavidin products interacting with the fluorescent biotin ligands (6) and (7). In the image, Lane 1 shows streptavidin incubated with fluorescently tagged mono-biotin ligand 7 in a 1:1 ratio at room temperature; Lane 2 shows streptavidin incubated with fluorescently tagged bisbiotin ligand 6 at room temperature; Lane 3 shows streptavidin with fluorescent dye (DBCO-Fluor 585 negative control); and Lane 4 shows streptavidin alone. The bands are located at the position where a 53 kD Molecular mass standard migrates to by gel electrophoresis. As indicated by the 53 kD band in Lane 2, the bisbiotin conjugate ligand (compound (6) of FIG. 4) can form a 1:1 complex with streptavidin.

Figure 7:
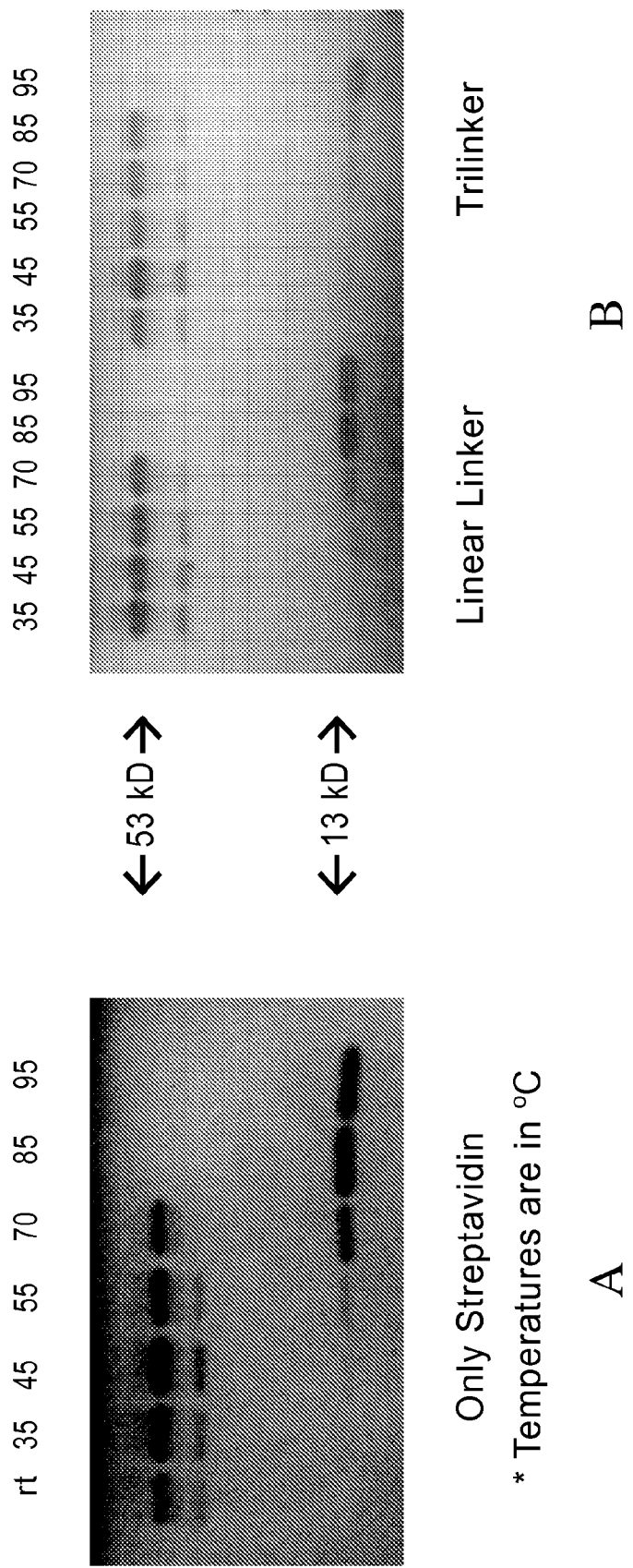
FIG. 7A shows an image of gel electrophoresis of streptavidin incubated alone at different temperatures.
FIG. 7B shows a gel electrophoresis image of complexes of streptavidin interacting with mono biotin ligand in a 1:4 ratio (8) and bisbiotin ligand in a 1:2 ratio (5a), which demonstrates that the bisbiotin complex is thermally more stable than the mono-biotin complex.
Figure 8:
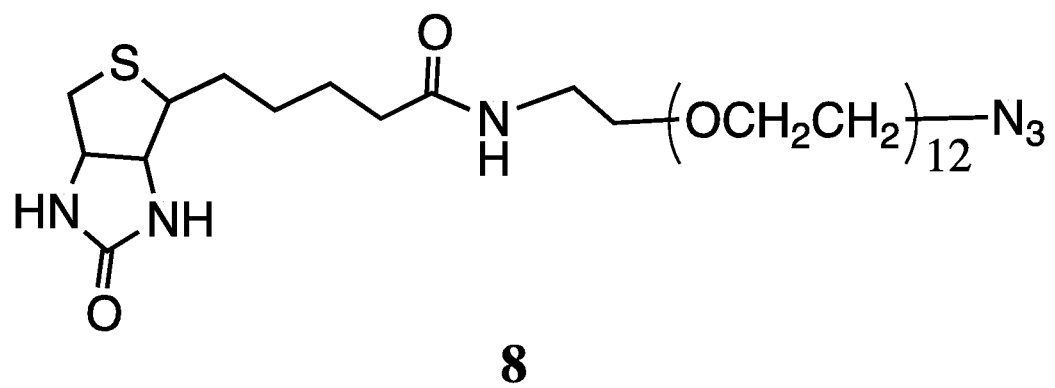
FIG. 8 shows the chemical structure of a monobiotin ligand (8).

In FIGS. 7A and 7B show the images from gel electrophoresis analysis of streptavidin and its complexes with mono biotin ligand (compound (8), shown in FIG. 8) and bisbiotin ligand (5a) (FIG. 1), which were incubated at different temperatures. In FIG. 7A, streptavidin alone was incubated at room temperature (rt), 35° C., 45° C., 55° C., 70° C., 85° C., and 95° C. Streptavidin is thermally stable up to 45° C. (the dark band corresponds to a 53 kD tetrameric streptavidin). At 55° C., a light band appears corresponding to 13 kD monomeric streptavidin. At 70° C., the intensity of the monomer band increases significantly. At the higher temperature (85° C.), the tetranieric streptavidin is completely disintegrated into its monomers.

FIG. 7B demonstrates that the thermal stability of streptavidin is increased by formation of complexes with biotins. When the streptavidin forms a 1:2 complex with the mono-biotin ligand (8) (structure shown in FIG. 8), indicated as "linear linker", streptavidin disintegration is reduced significantly at 70° C. However, the streptavidin is disintegrated completely at 85° C.

Importantly, there was a distinct difference in thermal stability of the streptavidin tetramer between a linear linker complex (compound (8) incubated with streptavidin) and the Y-shaped trilinker complex (in this example, compound (5a) incubated with streptavidin). When the streptavidin forms a 1:1 complex with the bisbiotin ligand (5a) (shown in FIG. 1) (equal to 2 equivalents of compound (8) in the number of effective biotin moieties), its complete disintegration takes place at 95° C. based on the gel electrophoresis, indicated as "trilinker" in FIG. 7B. Thus, the bisbiotin ligands of the instant disclosure are more thermostable than the mono-biotin ligands.

Atomic force microscopy (AFM) can be used to measure the mechanical force necessary to break the biotin-streptavidin interactions. The bisbiotin ligand (5b) is attached to an AFM tip through the method disclosed in U.S. Provisional Application Ser. No. 61/898,177. The attachment of biotin compounds of the present disclosure to AFM tip may include a PEG, or any other suitable linker known in the art. Streptavidin molecules are immobilized onto a mica substrate by a known method (See H. Wang et al., *Biophysical J.*, 2002, 83, 3619-3625). Immobilization of bisbiotin ligands on an AFM tip can be utilized for attaching streptavidin followed by biotinylated antibodies and other affinity molecules.

Figure 9:
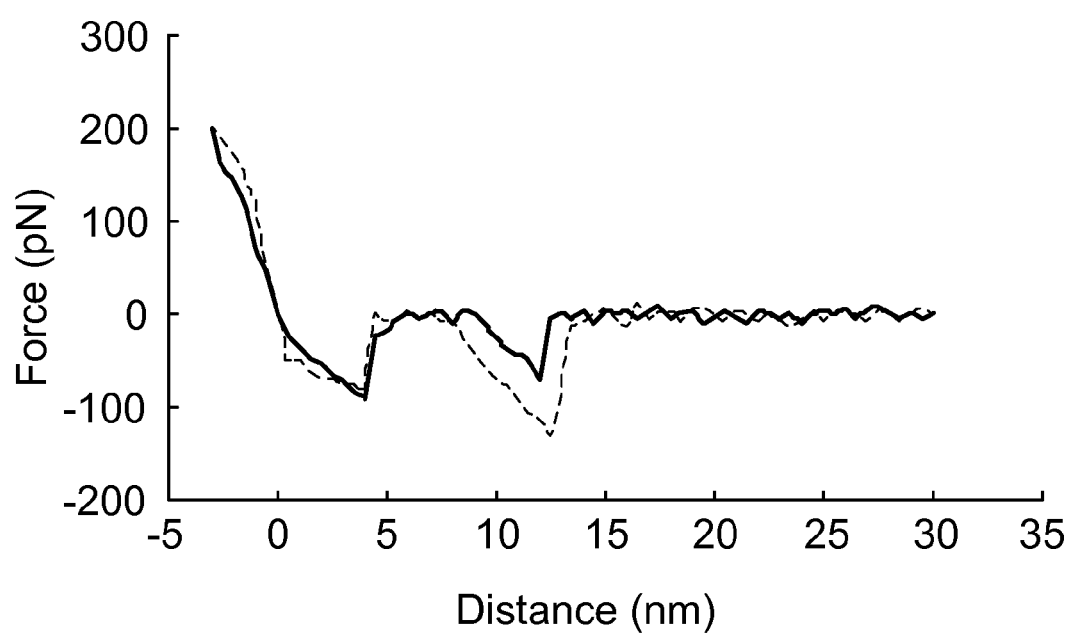
FIG. 9 shows a force distance curve of bisbiotin (5b) attached to an atomic force microscopy (AFM) tip. The solid line curve is a representative force distance curve of the mono-biotin unbinding from streptavidin immobilized on a mica substrate and the dotted line curve is a representative force distance curve of the bisbiotin (5b) unbinding from streptavidin immobilized on a mica substrate. The unbinding force of (5b) is larger than that of the mono-biotin ligand.
Figure 10:
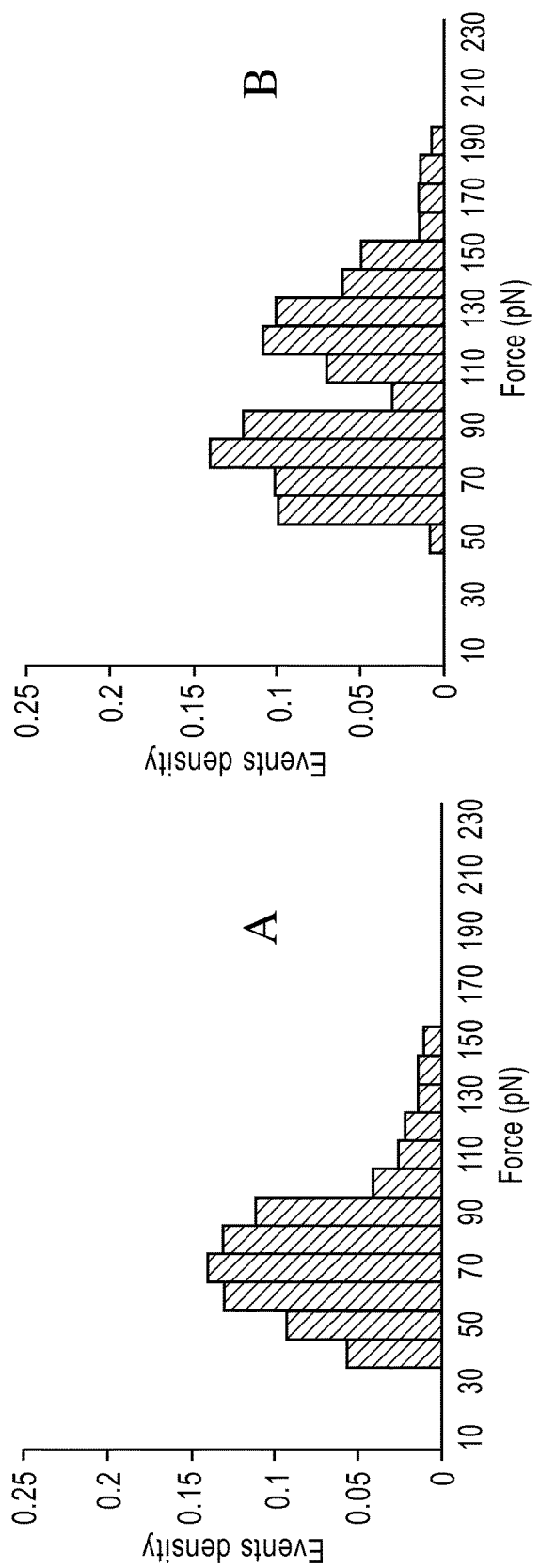
FIG. 10A shows a force histogram of monobiotin unbinding from the streptavidin immobilized on a mica substrate.
FIG. 10B shows a force histogram of bisbiotin unbinding from the streptavidin immobilized on a mica substrate.

FIG. 9 shows a representative force distance curve (dotted lines) of the bisbiotin ligand (5b) unbinding from the streptavidin immobilized on the mica substrate. As shown in this figure, the unbinding force of (5b) (see the rupture at the distance of ~13 nm) is larger than that of the mono-biotin ligand (solid line). In fact, the force histograms show that the mono biotin ligand has a force peak around ~68.5 pN (see FIG. 10A) and the bisbiotin ligand has two force peaks around ~70 pN and ~131 pN (see FIG. 10B). Accordingly, this study shows that the interaction of streptavidin with bisbiotin is much stronger than that with mono-biotin.

The bisbiotin ligands of the present disclosure can be immobilized on a solid surface. To demonstrate the relative utility of such immobilized mono and bisbiotin compounds, thiolated compounds were synthesized, as shown in FIGS. 11 and 12, immobilized on gold substrates, and subjected to surface plasmon resonance (SPR).

Figure 11:
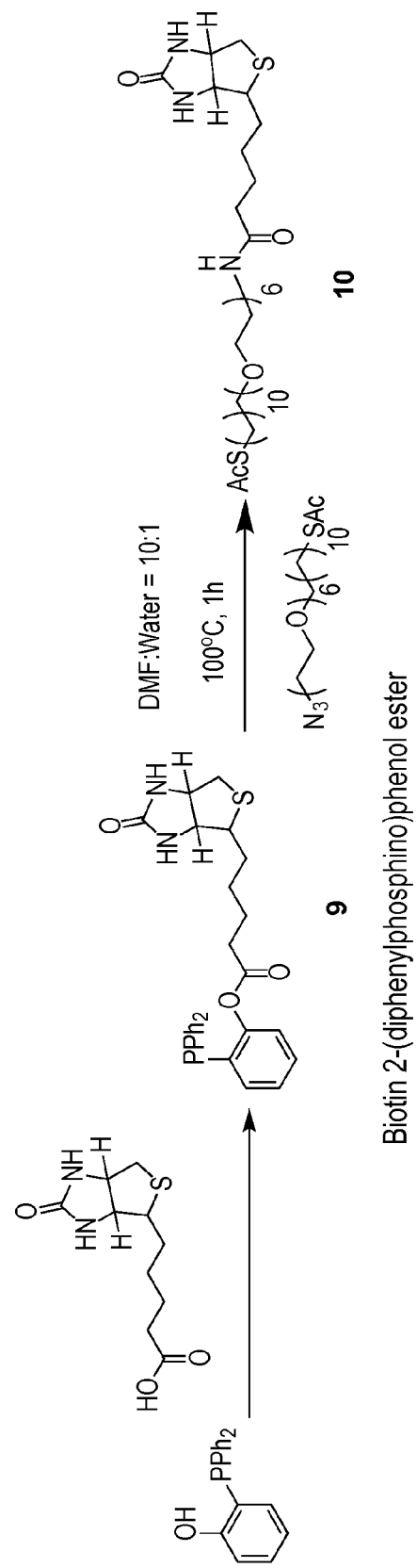
FIG. 11 shows the synthesis of mono-biotin with an alkylated PEG linker bearing a thioacetate end (10).

FIG. 11 shows the synthesis of a thiolated mono-biotin ligand (10). In the synthesis, biotin 2-(diphenylphosphino) phenolester (9) is synthesized as a precursor for reacting with azido molecules, for example, azido-PEG-alkyl-Sac.

Figure 12:
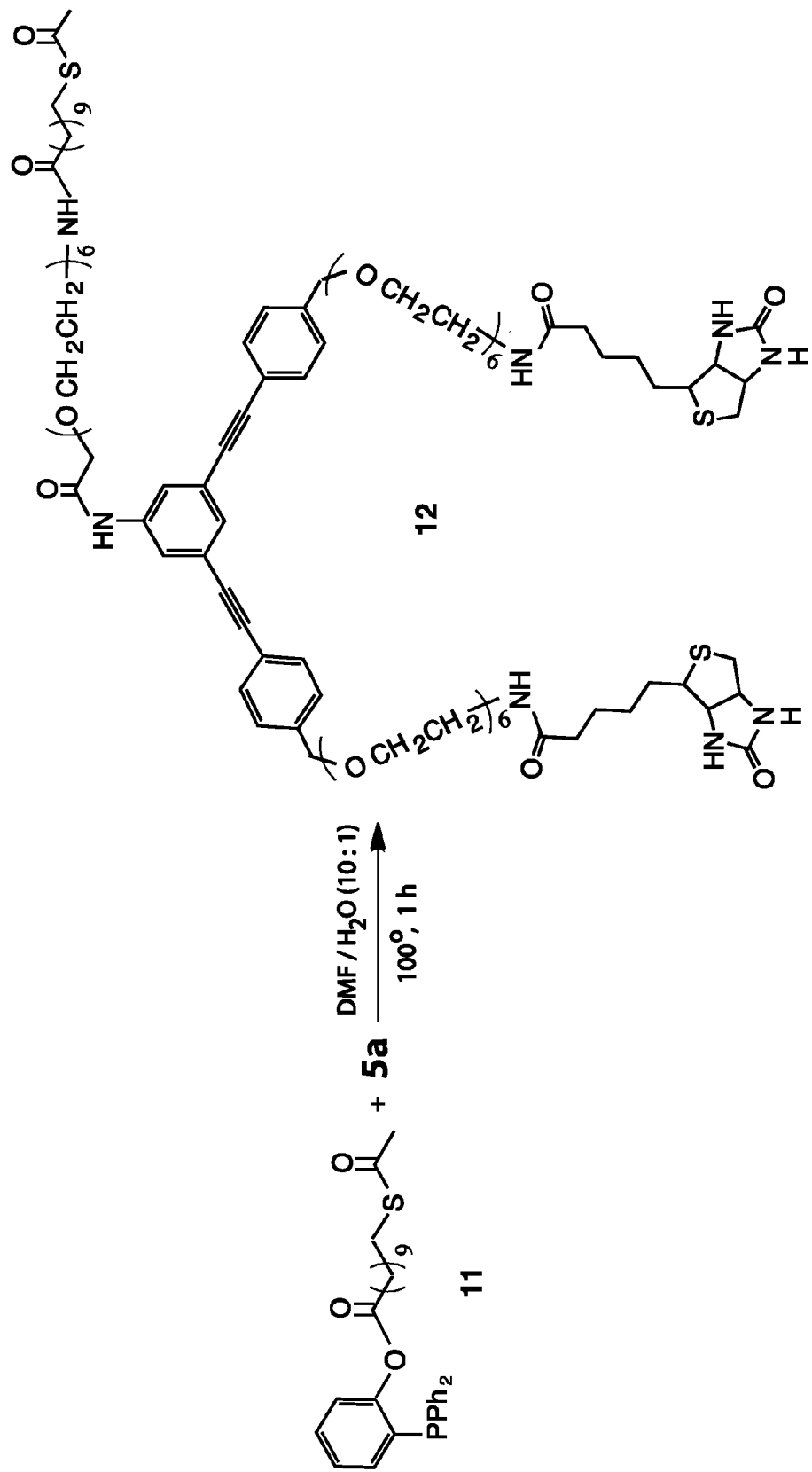
FIG. 12 shows the synthetic method for introducing an alkylated PEG linker bearing a thioacetate end to the three-arm bisbiotin ligand for immobilization of streptavidin on gold substrates.

FIG. 12 shows the synthesis of a thiolated bisbiotin ligand (12). Reacting the bisbiotin ligand (5a) with 10-(acetylthio) decanoic acid 2-(diphenylphosphino)phenol ester (11) yields a thiolated bisbiotin ligand (12).

Figure 13:
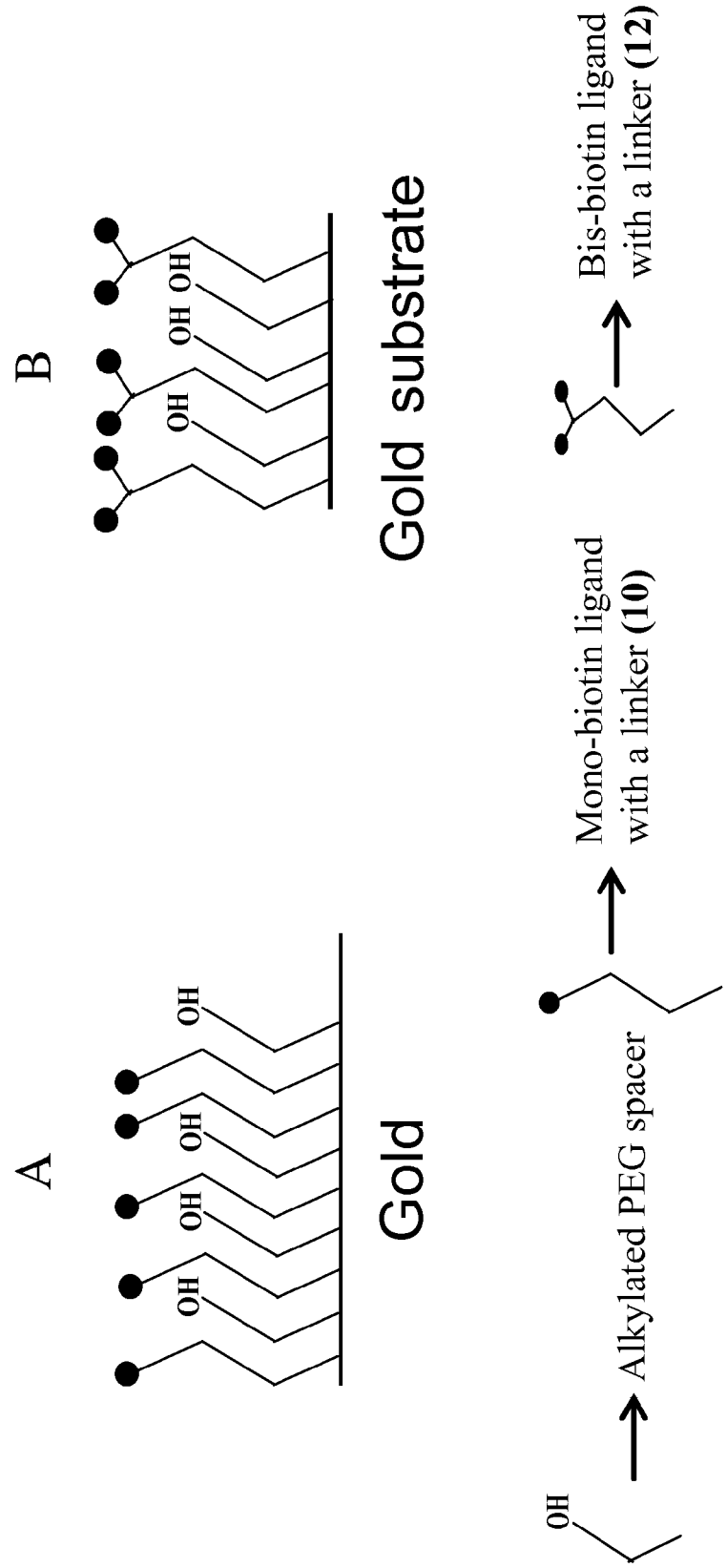
FIG. 13A shows an illustration of the structure of a mixed monolayer on gold substrates containing mono-biotin ligands (10).
FIG. 13B shows an illustration of the structure of a mixed monolayer on gold substrates containing bisbiotin ligands (12).

Mixed monolayers of the mono and bisbiotin compounds can be formed on gold substrates, as illustrated in FIGS. 13A and 13B. The mono-biotin ligand (10) forms mixed monolayers on a gold substrate in the presence of pyrrolidine, as illustrated in FIG. 13A, and the bisbiotin ligand (12) is used to form a mixed monolayer on a gold substrate in the presence of pyrrolidine as illustrate in FIG. 13B.

Figure 14:
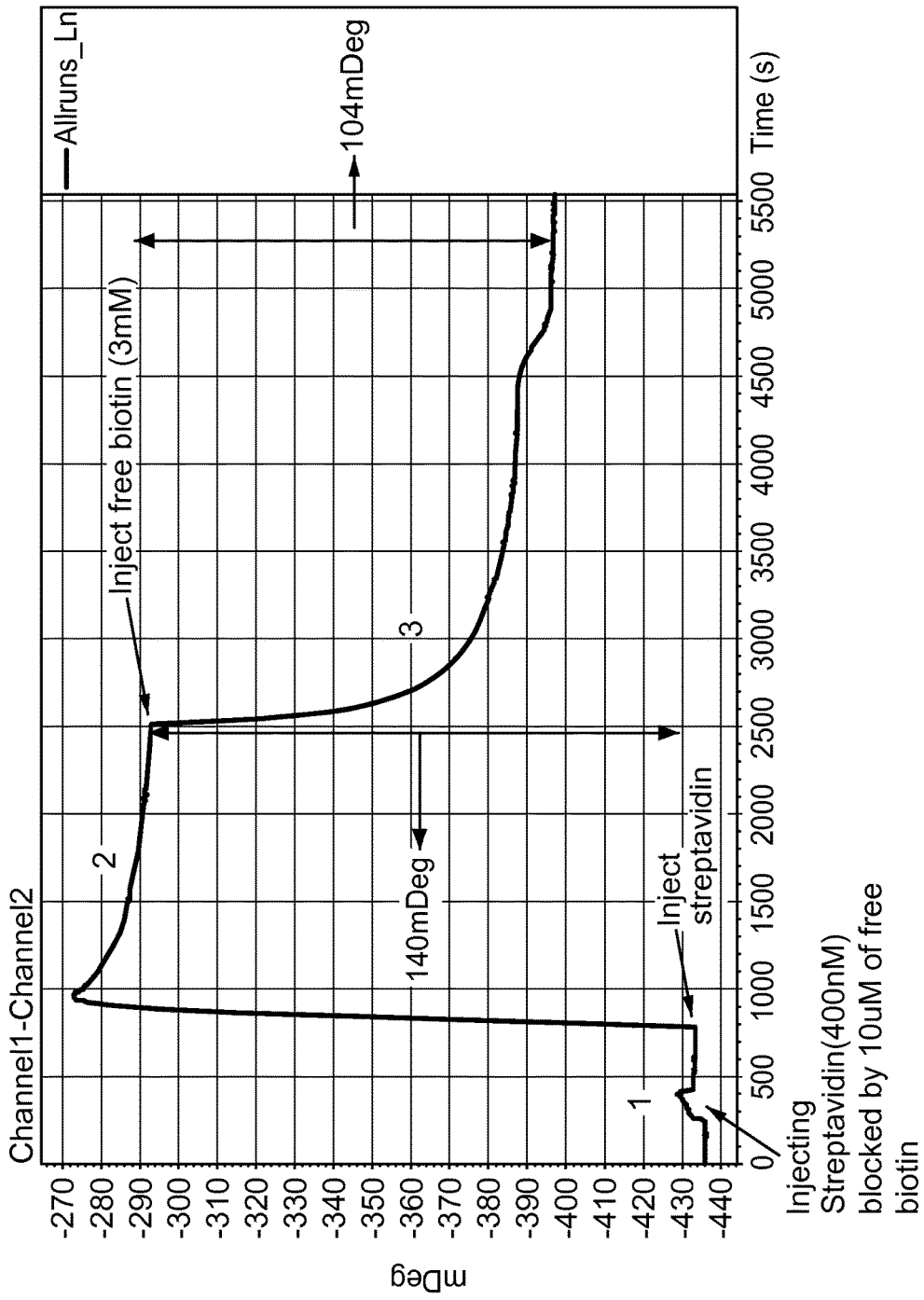
FIG. 14 shows a sensorgram of formation and dissociation of a streptavidin layer on a mixed monolayer of the mono-biotin on a gold substrate (10).

In one embodiment, a streptavidin layer is quickly formed after injecting a streptavidin solution onto the mono-biotin monolayer on a gold substrate through a surface plasmon resonance (SPR) flow cell. In FIG. 14, the SPR sensorgram shows that 74% of streptavidin is sharply dissociated from the surface after injecting a free biotin solution in a period of 27 minutes.

Figure 15:
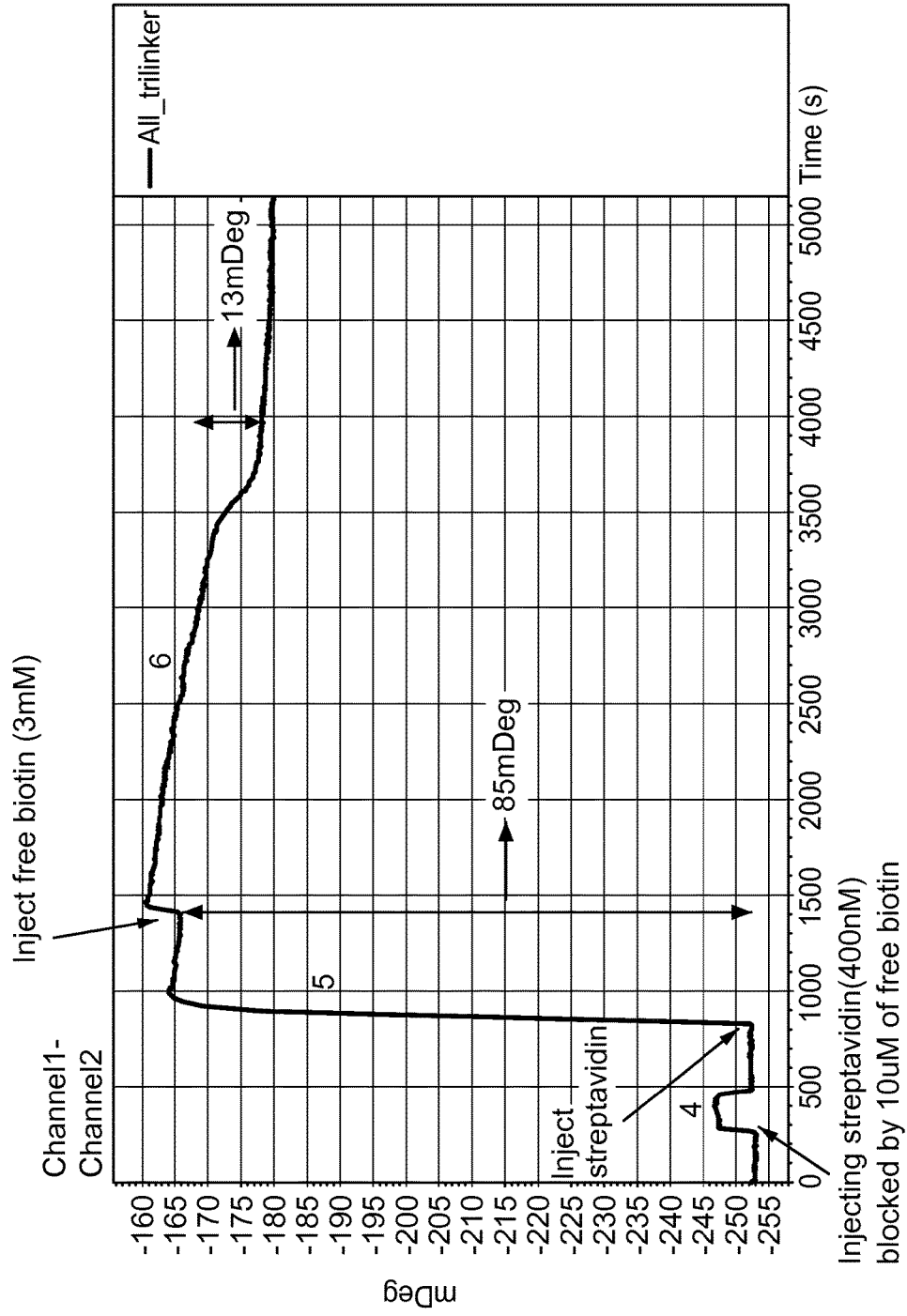
FIG. 15 shows a sensorgram of formation and dissociation of a streptavidin layer on a mixed monolayer of the bisbiotin on a gold substrate (12).

In another embodiment, a streptavidin layer is quickly formed after injecting a streptavidin solution onto the bis-biotin monolayer on a gold substrate through a SPR flow cell, In FIG. 15, the SPR sensorgram shows that 15% of streptavidin is dissociated very slowly after injecting the same amount of free biotin solution.

This exemplary data demonstrates the higher relative stability of bisbiotin bound streptavidin compared to mono-biotin bound streptavidin. The increased stability of the bisbiotin ligands of the present disclosure complexed to streptavidin provides the potential utility of the bisbiotin compounds of the present disclosure in assays and arrays that would benefit from immobilization on a substrate or film. Biotinylated DNA probes and antibodies can be attached to streptavidin that is immobilized through the bisbiotin on a solid surface without the streptavidin dissociating form the surface.

Likewise, any assays that have been developed using mono-biotin binding streptavidin may be improved by utilizing the bisbiotin compounds of the present disclosure. Such bisbiotin compounds in complex with streptavidin demonstrate increased thermal stability and slowed dissociation, as well as the ability to withstand greater mechanical force compared to prior art mono-biotin-streptavidin complexes. In fact, no other bisbiotin ligands reported in the literature have demonstrated the same thermal stability as that observed with the bisbiotin ligands described herein.

Moreover, the unique three-arm structure of the bisbiotin ligands described herein allows the connection of biomolecules to solid surfaces for detection, separation, and labelling through streptavidin binding, For example, embodiments of the disclosure demonstrate, for the first time, the use of a bisbiotin ligand to immobilize streptavidin on a gold substrate.

The details of one or more embodiments of the present disclosure are set forth in the accompanying description above and has been presented only for the purposes of illustration and is not intended to limit embodiments and inventions disclosed herein to the precise form disclosed. Any methods and materials similar or equivalent to those described herein can be used in the practice or testing of embodiments of the present disclosure. Still other embodiments of the present disclosure may be patentable over prior art references for expressly lacking one or more elements disclosed in the prior art (i.e., claims covering such embodiments may include negative limitations). Other features, objects, and advantages of embodiments of the present disclosure will be apparent from the description and from the originally filed claims (as well as claims supported by the present disclosure). In the specification and the appended claims, the singular forms include plural referents unless the context clearly dictates otherwise. Unless defined otherwise, all technical and scientific terms used herein have the same meaning as commonly understood by one of ordinary skill in the art to which embodiments of the present disclosure belong. All patents and publications cited in this specification are incorporated by reference.

The invention claimed is:

1. A ligand comprising a multiplicity of biotin moieties, wherein each biotin moiety is attached to a rigid, nano-meter central core through a flexible linker, wherein the ligand presents at least two biotin moieties to a target, and wherein the at least two biotin moieties are attached to a trilinker having the following structure:

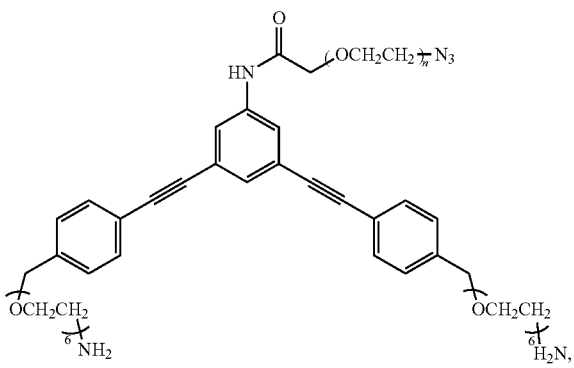

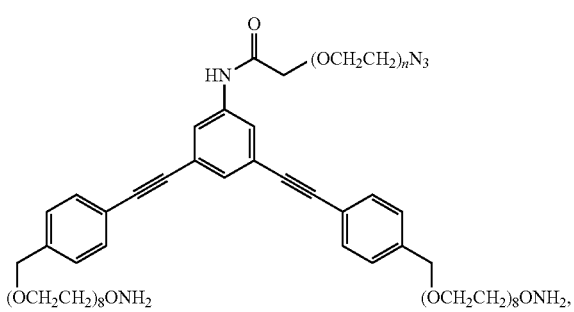

or

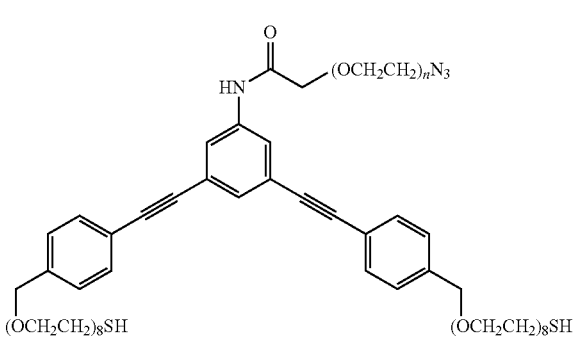

wherein n is 1 to 50.

2. The ligand of claim 1, wherein the target is streptavidin.

3. The ligand of claim 1, wherein n is 6.

4. The ligand of claim 1, wherein the ligand has the following structure

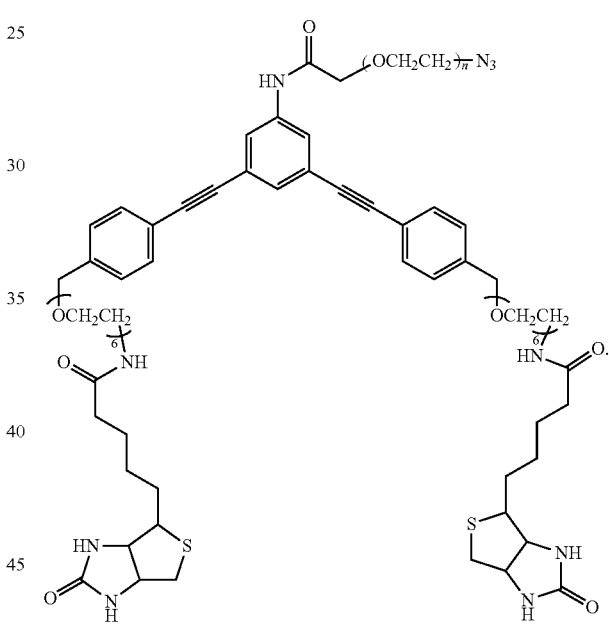

5. The ligand of claim 1, wherein the ligand is conjugated to a moiety selected from the group consisting of: a fluorescent tag, a quantum dot, a redox reagent, a magnetic nanoparticle, and a gold nanoparticle.

6. The ligand of claim 5, wherein the ligand has the following structure

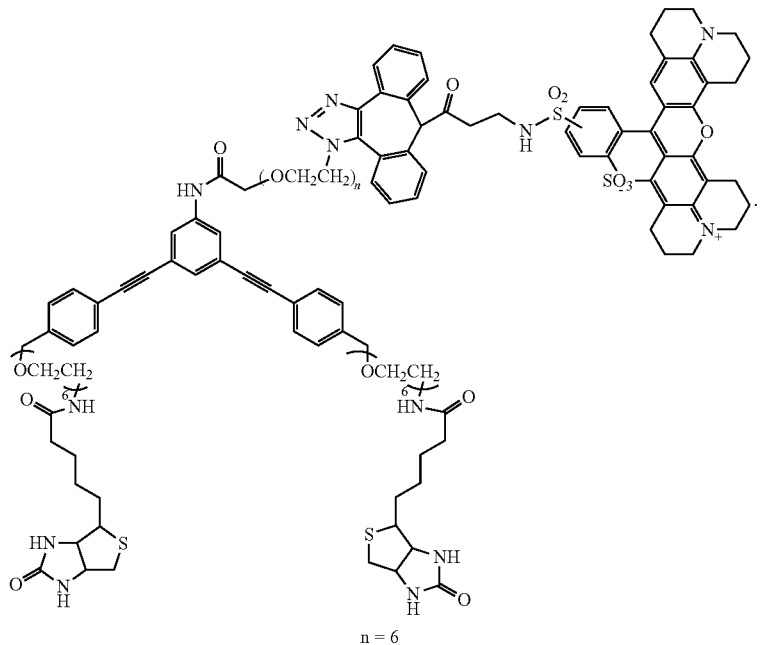

n = 6

7. The ligand of claim 1, wherein the ligand is immobilized to an atomic force microscopy tip.

8. The ligand of claim 7, wherein the ligand is connected to the atomic force microscopy tip via a PEG linker.

9. The ligand of claim 1, wherein the ligand is attached to a nanoparticle functionalized with alkynes through a reaction between the azide on the ligand and the alkynes.

10. A method for the separation and detection of biomolecules in a biological sample, the method comprising:
   immobilizing streptavidin to the ligand of claim 9 via streptavidin-biotin interaction;
   attaching one or more biotinylated probes or affinity molecules to the streptavidin to form a streptavidin/biotin nanoparticle complex, wherein the one or more biotinylated probes or affinity molecules are capable of binding to the biomolecules in the biological sample;
   incubating the nanoparticle complex with the biological sample under conditions to allow the one or more biotinylated probes or affinity molecules to bind to the biomolecules in the biological sample;
   separating the biomolecules bound to the nanoparticle complex from the biological sample; and
   detecting the binding of biomolecules to the nanoparticle complex.

11. The method of claim 10, wherein the biomolecule is selected from the group consisting of DNA, RNA, proteins, and peptides.

12. The method of claim 10, wherein the probes are DNA probes or RNA probes.

13. The method of claim 10, wherein the affinity molecules are one or more of antibodies, aptamers, or peptides.

14. The ligand of claim 1, further comprising a thiol group at a non-biotin moiety region of the ligand.

15. The ligand of claim 1, having the following structure:

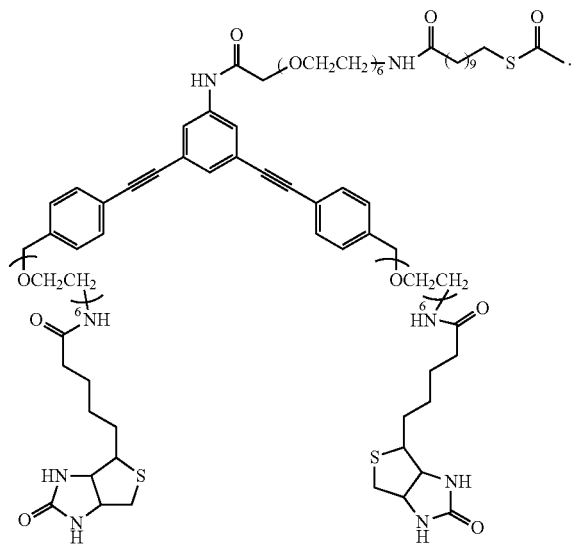

16. A monolayer comprising a plurality of the ligands of claim 14 immobilized on a gold substrate.

17. The monolayer of claim 16, wherein the monolayer further comprises an alkylated PEG spacer.

* * * * *